United States Patent [19]
Hench et al.

[11] Patent Number: 6,051,247
[45] Date of Patent: *Apr. 18, 2000

[54] MOLDABLE BIOACTIVE COMPOSITIONS

[75] Inventors: Larry L. Hench, London, United Kingdom; Guy LaTorre; Jon K. West, both of Gainesville, Fla.; June Wilson, London, United Kingdom; William Toreki, III; Christopher Batich, both of Gainesville, Fla.

[73] Assignee: University of Florida Research Foundation, Inc., Gainesville, Fla.

[*] Notice: This patent is subject to a terminal disclaimer.

[21] Appl. No.: 09/113,769

[22] Filed: Jul. 10, 1998

Related U.S. Application Data

[63] Continuation-in-part of application No. 08/657,713, May 30, 1996, Pat. No. 5,840,290
[60] Provisional application No. 60/052,169, Jul. 10, 1997.

[51] Int. Cl.[7] .............................. A61F 2/02; A61K 9/50; B32B 5/16; B32B 15/02; B32B 9/02
[52] U.S. Cl. .................. 424/423; 424/499; 428/402; 428/402.24
[58] Field of Search ................................ 424/423, 499; 428/402, 402.24

[56] References Cited

U.S. PATENT DOCUMENTS

| | | |
|---|---|---|
| 4,103,002 | 7/1978 | Hench et al. . |
| 4,159,358 | 6/1979 | Hench et al. . |
| 4,171,544 | 10/1979 | Hench et al. . |
| 4,189,325 | 2/1980 | Barrett et al. . |
| 4,234,972 | 11/1980 | Hencf et al. . |
| 4,775,646 | 10/1988 | Hench et al. . |
| 4,803,075 | 2/1989 | Wallace et al. . |
| 4,851,046 | 7/1989 | Low et al. . |
| 5,074,916 | 12/1991 | Hench et al. . |
| 5,204,382 | 4/1993 | Wallace et al. . |
| 5,263,985 | 11/1993 | Bao et al. . |
| 5,352,715 | 10/1994 | Wallace et al. . |
| 5,451,406 | 9/1995 | Lawin et al. . |
| 5,522,893 | 6/1996 | Chow et al. . |
| 5,840,290 | 11/1998 | Hench et al. ............... 424/423 |

OTHER PUBLICATIONS

Balazs, E. A. et al., "Block Coagulation and Fibrinolysis", *Matrix Engineering*, v2; p173–178, 1991.
Buckley, J. F. et al., Endoscopic Correction of Vesicoureteric Reflux with Injectable Microparticulate Silicone, "*The Journal of Urology*", v147–4; p356A, Apr., 1992.
Hench, L. L. et al., "Bonding Mechanisms at the Interface of Ceramic Prosthetic Materials", J. Biomed, Mater, Res. symposium, v2, (part 1) p117–141, 1971.
Hench, L. L., et al., "Direct Chemical Bond of Bioactive Glass–Ceramic materials to Bone and Muscle", J. Biomed, Mater. Res. Symposium, v4, p25–42, 1973.
Hench, L. L., et al., "Advanced Series in Ceramics", *An Introduction in Bioceramics*, World Scientific, v1; p 1–24, 1993.
Kirk–Othmer, "*Concise Encyclopedia of Chemical Technology*", p104–106, 1985.
*"Manufacture of artificial bones from powdery hydroxylapatite and dextran", Nagase, Japan, Kokei Tokyo Koho JP 63–189, 156, Aug. 1988.
*Rodriguez, et al., Optimization of the mechanical properties of dextran–based femoral plugs., "Congr. Int. Technol. Pharm.", 5th, 4, p376–390, 1989.
Schortliffe, L. M. K., et al., "The Treatment of Urinary Incontinence by the Periurethral Implantation of Glutaraldehyde Dross–linked Collagen", *The Journal of Urology*, v141; p538–541, 1989.
Schulman, C. C., Md. PhD., "Section on Urology Program for Scientific Sessions", *The Journal of Urology*, p85, Oct. 1992.
Walker, R. D. et al., "Injectable Bioglass as a Potential Substitute for Injectable Ploytetrafluroethylene", *The Journal of Urology*, v1, p65–67, Aug.1992.
*Wilson, J. et al., "Biomaterials for facial bone augmentation: Comparative studies", *Applied Biomaterials*, v22, (A2), p159–177, 1988.
Wilson, Low et al., Biomaterials and Clinical application, Ed. By Pizzoferrato, et al., Elsevier Science Publishers B. V. Amsterdam, 1987.
Wilson J., et al;., "Toxicology and biocompatibility of bioglasses", *Journal of Biomedical Materials Research*, v15, p805–817, 1981.

*Primary Examiner*—Carlos A Azpuru
*Attorney, Agent, or Firm*—Burns, Doane, Swecker & Mathis, L.L.P.

[57] ABSTRACT

A moldable bioactive composition including (a) bioactive particles of bioactive glass, glass-ceramics, calcium phosphates, calcium apatites, or mixtures thereof; and (b) a biodegradable polysaccharide carrier including a polysaccharide with an average molecular weight of about 200,000–5,000,000.

20 Claims, No Drawings

MOLDABLE BIOACTIVE COMPOSITIONS

This Application is a continuation-in-part application to pending U.S. Ser. No. 08/657,713 filed May 30, 1996, which has issued as U.S. Pat. No. 5,840,290 herein incorporated by reference in its entirety. This Application is also a non-provisional application claiming priority to U.S. Provisional Patent Application No. 60/052,169, filed Jul. 10, 1997, herein incorporated by reference in its entirety.

This invention was made with government support under U.S. Air Force Office of Scientific Research Grant Number F49620-92-0351 awarded by the United States Air Force. The government has certain rights in the invention.

FIELD OF THE INVENTION

The present invention generally relates to bioactive compositions. More particularly, the present invention relates to bioactive compositions with a polysaccharide carrier.

BACKGROUND OF THE INVENTION

The use of natural and synthetic bone grafting materials in reconstructive surgery has been well established. Autogenous bone is typically preferred for the repair of bony defects in a variety of dental and orthopedic clinical procedures. Although it is desirable to use autogenous bone for defect repair, it is often in limited supply and there are problems associated with the surgery to harvest these grafts. Allografts are a popular alternative to autografts for promoting osseous ingrowth. Although there is an abundance of these cadaver harvested grafts, allografts have their associated problems, including possible disease transmission, incomplete incorporation and lot to lot variability with respect to its capability to induce osseous in-growth. As a result, synthetic bone grafting materials have become popular for use in these types of procedures.

Many calcium phosphate based ceramics have been developed for use as bone grafting substitutes. Bioactive glasses and glass ceramics are examples of these synthetic bone grafting materials. Bioactive glasses and glass ceramics have been utilized as bone replacement materials in a variety of dental and orthopedic reconstructive surgical techniques. These glasses develop a strong bond with hard tissue due to a series of ion exchange reactions between the implant surface and body fluids that result in the formation of a biologically active calcium phosphate film at the implant tissue interface. See Hench et al, *J. Biomed. Mater. Res.*, Vol. 5, pp. 117–141 (1971), and Hench et at, *J. Biomed. Mater. Res.*, Vol. 7, pp. 25–42 (1973). Bioactive glasses also have been shown to form a firm bond with soft tissue. See Wilson, et al, *J. Biomed. Mater. Res.*, Vol. 15, pp. 805–817 (1981); Wilson and Merwin, *J. Biomed. Mater. Res.: Applied Biomaterials*, Vol. 22, No. A2, pp. 159–177 (1988); and Wilson, Low et al, *Biomaterials and Clinical Applications*, Ed. By Pizzoferrato et al, Elsevier Science Publishers B. V., Amsterdam (1987).

Certain bioactive and biocompatible glasses and glass-ceramics, e.g., those described in U.S. Pat. Nos. 4,159,358; 4,234,972; 4,103,002; 4,189,325; 4,171,544; 4,775,646; 4,851,046, and 5,074,916 (all incorporated herein by reference), have been shown to develop a unique, strongly adherent, chemical bond with hard tissue (bone). This is a result of the formation of a biologically active calcium phosphate (hydroxycarbonate apatite) film generated in situ by ion-exchange reactions between the glass or glass-ceramic surface and body fluids. This influence results in a strong fixation of the glass or glass-ceramic to the bone surface.

The particulate form of bioactive glasses has been used in the repair of periodontal defects in humans for several years. The material is usually mixed with sterile saline, or the patient's own blood, which forms a coherent mass and remains workable for several minutes before placement in the defect site. Although this approach works well for smaller defect sites, there is the need for filling larger defects where it is desirable to have a more malleable material that can be easily shaped and placed into the defect site. Such a material should be sufficiently cohesive to prevent the problems of particle migration associated with some particulate grafting materials. This type of moldable grafting material can be used in a variety of reconstructive surgical procedures including to orthopedic, maxillofacial and dental applications.

Several approaches to defect repair in these procedures include the use of natural and synthetic constituents to achieve the desired osteoconductive and handling properties described above. These graft materials may be in the form of a paste or putty, which either retains its malleable characteristics after implantation, or hardens in situ, similar to a cement. An example of the use of calcium phosphate based cements as a bone filling material is described in U.S. Pat. No. 5,522,893. This patent describes a combination of tetracalcium phosphate and dicalcium phosphate salts that are mixed and react to harden and form a hydroxycarbonate (HCA) apatite after implantation. Although the HCA that forms effectively fills the defect site, the material is not osteoconductive. The material is relatively insoluble in water and non-absorbable, being only partially replaced by natural bone tissue.

U.S. Pat. No. 5,263,985 ("the '985 patent") describes an implantable material for promoting bone growth which has a microporous structure exhibiting an average pore size of at least 30 Angstroms. The porous biomaterial is capable of retaining macromolecules having a molecular weight of at least 15,000 and up to 500,000. The '985 patent further describes the use of dextran beads having controlled pore size to stimulate bone and tissue growth. However, only negatively charged beads displayed an osteoinductive effect.

Dextrans have been used as femoral plugs. See Rodriguez et al., *Optimization of the mechanical properties of dextran-based femoral plugs, Congr. Int. Technol. Pharm.*, $05^{th}$ 1989, 4, 376–90 which describes compressed dextran powders for use as femoral bone plugs tested for their resistance to disintegration and for their plasticity as a function of molecular weight (17,200 to 5–40 million). Preliminary in vivo results showed that the plugs were completely absorbed at the end of 2 to 20 days.

Dextrans have also been combined with hydroxyapatite. See *Manufacture of artificial bones from powdery hydroxylapatite and dextran*, Nagase, Japan Kokei Tokyo Koho JP 63-189,156 Aug. 4, 1988. Hydroxyapatite is not class A bioactive. This article describes artificial bones and prosthetics prepared by mixing hydroxyapatite and dextran with or without water or saline solution. Saline was added to sterilized dextran and mixed with hydroxylapatite powder. The resulting plastic paste was added to bone's missing parts.

In the past, other carriers such as polymethylmethacrylate, glycol dimethacrylate, and polylactic dimethacyrate have been used as carriers for bioactive implant materials. However, these materials are not resorbable or degrade very slowly and are typically associated with soft tissue infiltration.

SUMMARY OF THE INVENTION

It is an object of the present invention to provide compositions and method for the repair, augmentation, reconfiguration or replacement of hard tissue structures which avoids many of the disadvantages associated with presently employed materials.

The present invention relates to moldable bioactive compositions including (a) bioactive particles of bioactive glass, glass-ceramics, calcium phosphates, calcium apatites, or mixtures thereof; and (b) a biodegradable polysaccharide carrier including a polysaccharide with an average molecular weight of about 200,000–5,000,000.

DETAILED DESCRIPTION OF THE INVENTION

The present invention is directed to moldable bioactive and biocompatible compositions with at least bioactive particles and a biodegradable polysaccharide carrier, for example, dextran, dextran sulfate, diethylaminoethyl dextran, or dextran phosphate or mixtures thereof. As the term "moldable" is used herein, it is intended to describe compositions that have sufficient viscosity such that they are not readily injectable into a patient with a standard needle with an opening smaller in diameter than 17 guage. Moldable compositions in accordance with the invention may also take the form of a paste.

Applicants have discovered that the use of polysaccharides with bioactive particles provides a surprisingly good implant material. The polysaccharide component is absorbed over time and the particulate glass remains at the selected anatomic structures and bonds uniformly throughout the particulate surfaces thereof with the tissue (bone) at the anatomic structures to provide anatomic integrity and to enhance osseous ingrowth. Polysaccharides such as dextrans are particularly well adapted for such use because the rate at which these materials are resorbed is complementary to the formation of HCA. The benefits of this balance are extensive. For example, when filling bone defects, soft tissue infiltration is ameliorated. Moreover, polysaccharides such as dextrans are particularly well adapted at maintaining even dispersion of the bioactive particles within the dextran such that over compression of the bioactive particles into the defect site preventing fluid diffusion into the particle mass, which may result in an unfavorable biological result, is avoided.

A biodegradable polysaccharide carrier is any polysaccharide capable of resorbing over time when implanted into a patient such as, for example, dextran, dextran sulfate, diethylaminoethyl dextran, or dextran phosphate or mixtures thereof. Biodegradable polysaccharide carriers in accordance with the present invention preferably include a liquid diluent such as deionized water in amounts in a weight of polysaccharide to volume of diluent of about 1:2 up to about 2:1. Lower molecular weight polysaccharides are cleared from the body faster that those of higher molecular weight. This behavior can be advantageous with respect to the present invention: if it desired that the dextran remain in the site for an extended period, dextrans of relatively high molecular weight may be used. The use of lower molecular weight dextrans have the advantage of a faster dextran absorption rate, resulting in earlier exposure of the bioactive glass particulate for reaction with the surrounding tissues. During the in vivo analysis however (specifically Example 5 below), an unexpected finding was that if one uses a dextran of too low a molecular weight, the dextran prevents clotting, resulting in deleterious hematoma formation. Use of higher molecular weights eliminates the potential complication of hematoma formation.

The term "viscous solution" as used herein means any moldable or semi solid composition, including highly viscous compositions sometimes referred to as "pastes or putties." As used herein, the term "animal" means mammal including a human. Unless specified otherwise the term "patient" means a human patient. The term "pharmaceutically acceptable" as used herein is consistent with the art and means compatible with the other ingredients of a pharmaceutical composition and not deleterious to the recipient thereof, The term "syringe" means any surgical instrument such as a cement gun, which is standard in the industry, with an opening whose diameter is larger than that of a 17 gauge syringe.

The term "anatomic structure" refers to any site or locus composed of hard tissue (bone) and/or soft tissue within the body of an animal. The term "anatomic integrity" refers to the desired size, shape or configuration of a particular anatomic structure after bonding therewith of the particulate glass phase of the composition of the present invention.

Anatomic structures treatable according to the method of the present invention include, but are not limited to maxilla, mandible, temporomandibular joint, chin, zygomatic arch, nose, ear, tooth root canal, tooth pulp caps, dental restoration; and osseous defects in the appendicular and axial skeleton, including long bones, vertebral spaces and around articulating joints.

One embodiment of the present invention is a pharmaceutically acceptable moldable, semi-solid or solid composition capable of being placed by hand or via a surgical syringe into a defect site, comprising a homogenous mixture of bioactive and biocompatible glass particulate composition having particle size from about 1000 $\mu$m to about 10 $\mu$m in a viscous solution of dextrans or of dextran derivatives having an average molecular weight of about 200,000 to about 5,000,000 daltons and optionally, one or more material enhancing agents, including preservatives, colorants, and flow enhancing, thickening or suspension agents. This invention is particularly useful in the repair, replacement, reconfiguration, reconstruction or augmentation of selected tissue (bone) anatomic structures. The ratio of particulate glass to the viscous solution in the suspension is such that the composition has the ability to be moldable and remains in place after placement.

As noted above, in the discussion of the background of this invention, bioactive and biocompatible material, especially ceramic and glass material, are known in the art of medicine as useful in the restoration of bone and soft tissue. This art is discussed extensively in *Introduction to Bioceramics*, Ed., L. L. Hench and J. Wilson, especially chapter 1, World Scientific, London (1993). Generally, it has been found that bioactive and biocompatible glasses having the following weight percent compositions give satisfactory results when utilized as the particulate glass component of the invention.

| Component | Mole Percentage |
|---|---|
| $SiO_2$ | 40–86 |
| CaO | 15–46 |
| $Na_2O$ | 0–35 |
| $P_2O_5$ | 1–8 |
| $CaF_2$ | 0–25 |
| $B_2O_3$ | 0–10 |

The bioactive particulate glass used in the present invention may be prepared according to the methods of the art such as taught in U.S. Pat. Nos. 4,159,358; 4,234,972; 4,103,002; 4,189,325; 4,171,544; 4,775,646; 4,851,046, and 5,074,916. For example, the raw materials (e.g., $SiO_2$, CaO, $Na_2O$ and $P_2O_5$) are mixed in plastic containers on a ball mill for four hours. The mix is then melted in a platinum crucible at 1350° C. and homogenized for 24 hours. The molten glass is poured into distilled, de-ionized water to produce a glass frit. The frit is ground in a mortar and pestle and passed through ASTM sieves to produce the required particle size range. The resulting particle size range, using this process, is then confirmed by optical microscopy, scanning electron microscopy, laser light scattering (Coulter LS 100), or other similar direct measurement technique.

The following compositions of bioactive glasses, known by the trademark "Bioglass" licensed to US Biomaterials, One Progress Boulevard, #23, Alachua, Fla., 32615, have been found to yield particularly good results and are, therefore, preferred.

TABLE 1

| Bioglass (Trademark) Bioactive Glass Compositions in Mole % | | | | |
| --- | --- | --- | --- | --- |
| Composition | $SiO_2$ | $Na_2O$ | CaO | $P_2O_5$ |
| 45S5 | 46.1 | 24.4 | 26.9 | 2.6 |
| 52S4.6 | 52.1 | 21.5 | 23.8 | 2.6 |
| 55S4.3 | 55.1 | 20.1 | 22.2 | 2.6 |

Other bioactive particles that may be used in accordance with the present invention include bioactive particles of glass ceramics, calcium phosphates, and calcium apatites. These bioactive particles are well known to those of ordinary skill in the art.

Dextrans are polysaccharides of D-glucose and are commercially produced by *Leuconostoc mesenteroides* and *L-dextranicum* bacteria. Dextrans have been widely used as plasma substitutes and blood extenders and are considered fully biocompatible and are metabolized in the body. Dextrans are available in a wide range of average molecular weights varying from 4,000 to 40,000,000 daltons and vary in rates of resorption in vivo for two to twenty days depending on the molecular weight. The use of dextran derivatives, including but not limited to diethylaminoethyl dextran and dextran sulfate, with bioactive glass is also within the scope of the present invention.

Dextrans and dextran derivatives useful in the present invention have molecular weights in the range of about 200,000 to about 5,000,000 daltons, preferably in the range of about 200,000 to about 1,000,000.

In addition to bioactive glass, polysaccharides and sterilized de-ionized water, the composition of the present invention optionally contain additives used in the pharmaceutical art to improve its performance and extend its shelf life. These additives include, but are not limited to, preservatives, colorants, and flow and suspension enhancing agents.

The compositions of the present invention may be conveniently prepared in one form by dissolving a polysaccharide such as dextran powder in a diluent (preferably sterile and de-ionized) to form a solution of desired viscosity which is suitable for use. The ratio of dextran to water will vary according to the molecular weight of the dextran but will be in the range of, for example, about one to four parts dextran to one part water by weight. The resultant viscous aqueous dextran then may be mixed with bioactive glass particles in, for example, the ratio of about one part dextran to about one to three parts bioactive glass (by weight) to form a viscous solution or putty which is moldable.

Alternatively, the compositions may be prepared by mixing the polysaccharide and bioactive glass powders directly. The mixed powders would then be mixed with an appropriate amount of sterile water or other appropriate fluid to form the viscous solution of the desired viscosity.

Additionally, the compositions may be prepared by premixing the polysaccharide, bioactive glass and fluid medium to produce a viscous solution, shaping this mixture to a predetermined shape and drying this resultant shape via freeze-drying or other suitable technique to produce a solid preform. This solid preform may then be supplied to the medical practitioner, at which time the preform is rehydrated, shaped as desired, and implanted.

Because the viscosity and, hence moldability, is a function of the ratio of glass to polysaccharide, this ratio will vary according to application and the preference of the medical practitioner. The prepared viscous composition may be marketed in several viscosities. Further, the practitioner can reduce the viscosity of the prepared solution at the time of insertion by the use of additional fluid. This fluid may include, but is not limited to, sterile water, more dextran, or more preferably, the patient's blood to add autologous osteogenic factors The fluid compositions of the present invention may be placed directly into the defect site by hand, or may be injected using a standard or modified medical syringe or other hardware into the site requiring repair or augmentation. The amount of material used is determined by the professional judgment of the medical practitioner treating the patient. After placement, the polysaccharide will begin to degrade and be removed from the site via normal cellular, fluid transport, and enzymatic action. Degradation and removal of will be essentially complete within about two days to three weeks after implantation, with lower molecular weight polysaccharides being removed at a higher rate than higher molecular weight polysaccharides. Upon removal of the polysaccharide component, the bioactive glass component will remain in the graft site. The bioactive glass particles bond to the hard and soft tissues at the site and create a long-lasting augmentation of the tissue. In a hard tissue site, the particles of glass will react and bond to existing bone and induce the formation of new bone, which will infiltrate the site.

The following examples are offered as illustrations of the present invention and are not to be construed as limitations thereof.

EXAMPLE 1

Forty grams of dextran of average molecular weight of about 400,000 to about 500,000 daltons was stirred into 50.0 cc of de-ionized water to form a viscous solution. The dextran water solution was loaded into a mixing syringe and sterilized by heating at 115° C. for 35 minutes. Five milliliters of the resultant solution was then mixed by hand with 10.0 cc bioactive glass, composition 45s5, having particle size of about 710 μm to about 90 μm, to form a moldable paste of uniform consistency.

EXAMPLE 2

A moldable solution is prepared as in Example 1 except that benzyl alcohol is added as a preservative at the rate of 0.05% % by weight prior to storing under sterile conditions. Handling properties were similar to those noted in Example 1.

EXAMPLE 3

A moldable solution is prepared as in Example 1 except that the composition of the bioactive glass is Bioglass 52s4.6. Handling properties were identical to those noted in Example 1.

EXAMPLE 4

An in vitro evaluation of dextran as a moldable vehicle was accomplished by mixing a series of different molecular weight dextrans (150,000, 464,000 and 2,000,000 daltons, Sigma Scientific, St. Louis, Mo.) and de-ionized water to achieve a desired viscosity. These solutions then were mixed with a desired amount of Bioglass (trademark) 45s5 particles to form a putty. The mixtures were molded by hand and placed in a simulated defect site of 6.0 mm diameter, created in a bovine femur. The mixtures were evaluated with respect to moldability, cohesiveness, and ease of placement at the site.

The following table summarizes the results of the evaluation of the resulting seven dextran/Bioglass® mixtures:

TABLE 2

| Sample | MW Dextran | Wt. Dextran/ Volume DI | Volume Dextran/ Volume Glass | Consistency |
|---|---|---|---|---|
| #1 | 150,000 | 6.0 g./5.0 cc | 5.0 cc/5.0 cc | Sticky, slightly moldable, flows easily. Difficult to place in defect by hand. |
| #2 | 150,000 | 5.0 g./2.5 cc | 2.5 cc/5.0 cc | Sticky, moldable, retains shape fairly well. Easy to place in defect but flows less easily. |
| #3 | 464,000 | 3.0 g./5.0 cc | 2.5 cc/5.0 cc | Sticky, moldable, flows readily when placed in defect. |
| #4 | 464,000 | 3.0 g./5.0 cc | 2.5 cc/7.5 cc | Dry, not readily moldable, does not flow. Does not stick to walls of defect. |
| #5 | 464,000 | 4.0 g./5.0 cc | 5.0 cc/10.0 cc | Sticky, very moldable, retains shape very well. Easy to place in defect. |
| #6 | 2,000,000 | 2.5 g./5.0 cc | 2.5 cc/5.0 cc | Slightly sticky, moldable, retains shape fairly well. Easy to place in defect |
| #7 | 2,000,000 | 2.5 g./5.0 cc | 2.5 cc/7.5 cc | Dry, not readily moldable, does not flow. Does not stick to walls of defect. |

The results show that Samples #5 and #6 produced mixtures that were easily molded and placed into the test site by hand. The mixtures were cohesive and tacky, tending to stick to the defect walls. These samples were prepared using dextrans of molecular weights of 464,000 dalton (Sample #5) and 2,000,000 dalton (Sample #6) in different concentrations and a bioactive glass content of 67% by volume. Increasing the glass content to 75% as for Samples #4 and #7 produced drier materials. These compositions became moldable on the addition of more fluid, in this case a few drops of deionized water being added. Use of the 150,000 dalton dextran (Samples #1 and #2) or lower concentrations of the 464,000 dalton dextran (Sample #3) produced mixtures having a viscosity suitable for injection through a syringe.

EXAMPLE 5

In an early animal study, eighteen New Zealand White rabbits were implanted with a mixture of 150,000 dalton dextran (3 grams dextran in 5 cc water) and 710 $\mu$m–90 $\mu$m 45s5 bioactive glass particulate in a volume ratio of one part dextran to 3 parts bioactive glass. Six-mm diameter defects were created bilaterally in the distal femurs of the rabbits and filled with the graft mixture. During the procedure, it was noted that the material was difficult to place and did not stay in the defect. Profuse bleeding was noted at the defect sites and two days after surgery, all animals had hematomas and swelling around the defect sites. At ten days, all animals were destroyed due to excessive drainage and pain.

EXAMPLE 6

Forty New Zealand White rabbits were implanted with a series of graft materials to evaluate the effect of the presence of 464,000 dalton dextran on bone formation in a critical size femoral defect (6 mm diameter). This defect is termed critical sized since an unfilled control defect will not heal even after six months. The following graft materials were evaluated:

1 Autogenous bone
2 Particulate Bioglass®
3 Particulate Bioglass® with 500,000 daltons dextran
4 Particulate Bioglass® with Autogenous bone(50:50)
5 Particulate Bioglass® with Autogenous bone(50:50) with 500,000 daltons dextran Samples #3 and #5 were identical to samples #2 and #4, respectively, with the exception of the addition of the dextran solution. This dextran solution (3.0 grams 464,000 daltons dextran to 5.0 grams water) was mixed with 710 $\mu$m–90 $\mu$m 45s5 bioactive glass particulate in a volume ratio of one part dextran to three parts bioactive glass. These samples were similar to Sample #4 in Example 4 and were mixed with small quantities of the blood from the surgical site at the time of implantation for easier handling. Six-mm diameter defects were created bilaterally in the distal femurs of the rabbits and manually filled with the graft materials. Eight animals were used for each test material and were left to heal for periods of 1, 2, 3, 6, and 12 weeks. No hematoma formation was noted over the course of the study. At sacrifice, the defect sites were evaluated using radiography, histology, and histomorphometric analysis. The results indicated no differences between the samples containing dextran and those without dextran in terms of cellular reaction or inflammation at one week. At two weeks, the only difference noted was a decrease in new bone tissue infiltration at two weeks for samples containing dextran (Samples #3 and #5), although this infiltration exceeded 50% for all graft materials. By four weeks, however, bone ingrowth had increased for the all dextran-containing samples such that ingrowth equaled that from the non-dextran-containing samples, indicating complete absorption of the dextran. That ingrowth equaled that of the autogenous graft sites demonstrates that the graft material containing dextran is as effective in filling bone defects as the gold standard of autogenous bone grafting. By comparison, the unfilled controls showed little or no bone ingrowth within this same time.

We claim:

1. A moldable bioactive composition comprising:
   (a) bioactive particles of bioactive glass, glass-ceramics, calcium phosphates, calcium apatites, or mixtures thereof, and;
   (b) a biodegradable polysaccharide carrier including a polysaccharide with an average molecular weight of about 200,000–5,000,000.

2. The bioactive composition of claim 1, further comprising a colorant, preservative, flow enhancer, or suspension enhancer, or mixtures thereof.

3. The bioactive composition of claim 1, wherein the polysaccharide carrier includes a diluent.

4. The bioactive composition of claim 3, wherein the diluent is deionized water.

5. The bioactive composition of claim 1, wherein said particles include particles up to about 1000 μm.

6. The bioactive composition of claim 1, wherein said particles include particles between about 90 μm to about 710 μm.

7. The composition of claim 1, wherein said bioactive glass particles comprise the following composition:

| Component | Mole Percentage |
|---|---|
| $SiO_2$ | 40–86 |
| CaO | 15–46 |
| $Na_2O$ | 0–35 |
| $P_2O_5$ | 1–8 |
| $CaF_2$ | 0–25 |
| $B_2O_3$ | 0–10 |

8. The composition of claim 1, wherein said polysaccharide is dextran, dextran sulfate, diethylaminoethyl dextran, or dextran phosphate or mixtures thereof.

9. The composition of claim 5, wherein said polysaccharide has an average molecular weight of about 300,000–2,000,000.

10. The biocompatible pharmaceutical composition of claim 5, wherein said polysaccharide has an average molecular weight of about 450,000–550,000.

11. The composition of claim 1, with substantially no amount of collagen.

12. The composition of claim 1, wherein the biodegradable polysaccharide carrier and the bioactive particles are present in a volume to volume ratio of about 1:3 to about 3:1.

13. The composition of claim 12, wherein said polysaccharide carrier includes a diluent.

14. The composition of claim 13, wherein said diluent is water.

15. The composition of claim 13, wherein said diluent is present in a diluent to polysaccharide ratio of about 1:3 to 3:1.

16. The composition of claim 1, wherein the biodegradable polysaccharide carrier and the bioactive particles are present in a volume to volume ratio of about 1:2.

17. A moldable bioactive composition for repair, replacement, reconfiguration, reconstruction or augmentation of selected hard tissue anatomic structures in a patient in need thereof comprising (a) bioactive particles of bioactive glass, glass-ceramics, calcium phosphates, calcium apatites, or mixtures thereof and (b) a biodegradable polysaccharide carrier, dextran, dextran sulfate, diethylaminoethyl dextran, or dextran phosphate or mixtures thereof.

18. A method for repair, replacement, reconfiguration, reconstruction or augmentation of selected hard tissue (bone) anatomic structures in a patient in need thereof, comprising repair and/or augmentation of hard tissue (bone) of said patient a homogenous suspension of bioactive and biocompatible glass particulate composition having particle size from about 710 μm to about 90 μm in an aqueous solution of dextrans or of dextran derivatives having an average molecular weight of about 500,000 daltons and optionally one or more preservative, coloring, flow enhancing, or suspension enhancing agents.

19. A method for inducing osteogenesis comprising contacting a patient in need thereof with an effective osteogenic amount of a mixture of:
   (a) bioactive particles of bioactive glass, glass-ceramics, calcium phosphates, calcium apatites, or mixtures thereof;
   (b) a biodegradable polysaccharide carrier including a polysaccharide with an average molecular weight of about 200,000–5,000,000.

20. The method of claim 19, wherein said biodegradable polysaccharide carrier includes a diluent in a polysaccharide to diluent ratio of about 1:3 to 3:1.

* * * * *